United States Patent
Jamnia et al.

(10) Patent No.: US 7,159,494 B2
(45) Date of Patent: Jan. 9, 2007

(54) TORQUE LIMITING WRENCH FOR ULTRASONIC SCALER TIP INSERTION

(75) Inventors: Mohammad A. Jamnia, Chicago, IL (US); Patricia H. Parker, Midlothian, IL (US); William L. Bollig, Elk Grove Village, IL (US); Chadd Berkun, Highland Park, IL (US); Marjavis J. Matthis, Chicago, IL (US)

(73) Assignee: Hu-Friedy Mfg. Co., Inc., Chicago, IL (US)

( * ) Notice: Subject to any disclaimer, the term of this patent is extended or adjusted under 35 U.S.C. 154(b) by 0 days.

(21) Appl. No.: 11/275,086

(22) Filed: Dec. 8, 2005

(65) Prior Publication Data

US 2006/0123958 A1 Jun. 15, 2006

Related U.S. Application Data

(60) Provisional application No. 60/635,761, filed on Dec. 14, 2004.

(51) Int. Cl.
*B25B 23/14* (2006.01)

(52) U.S. Cl. .............. 81/467; 81/472; 81/478; 81/480

(58) Field of Classification Search ........... 81/467, 81/472, 478, 480
See application file for complete search history.

(56) References Cited

U.S. PATENT DOCUMENTS

| | | | |
|---|---|---|---|
| 2,800,816 A | 7/1957 | Tasciotti | 81/3.34 |
| 3,142,211 A | 7/1964 | Faso | 81/125 |
| 4,131,039 A | 12/1978 | Garconnet | |
| 4,679,468 A | 7/1987 | Gray | |
| 5,059,210 A | 10/1991 | Clark et al. | 606/169 |
| 5,179,617 A | 1/1993 | Stockman | |
| 5,287,775 A | 2/1994 | Moore | |
| 5,571,014 A | 11/1996 | Gregory, Jr. et al. | |
| 5,779,409 A * | 7/1998 | Manzolli | 411/7 |
| 5,857,816 A | 1/1999 | Assmundson | |
| 6,308,598 B1 | 10/2001 | O'Neil | |
| 6,807,885 B1 | 10/2004 | Loper | |
| 2003/0054318 A1 | 3/2003 | Gervais et al. | |
| 2004/0055425 A1 | 3/2004 | Casabonne et al. | 81/64 |

(Continued)

FOREIGN PATENT DOCUMENTS

DE 90 03 771.5 6/1990

(Continued)

OTHER PUBLICATIONS

European Search Report form European patent application No. EP 05 25 7666, dated May 11, 2006.

*Primary Examiner*—Lee D. Wilson
*Assistant Examiner*—Shantese McDonald
(74) *Attorney, Agent, or Firm*—Marshall, Gerstein & Borun LLP

(57) ABSTRACT

A torque wrench for preventing transmission of torque in excess of a threshold level to avoid damage to replaceable scaler tips and hand pieces of ultrasonic dental instruments. The torque wrench has a housing with a core seated therein, with a cam mechanism or spring engagement between the core and the housing, such that the core may remain stationary when the housing is rotated passed the threshold level of torque. The core has an axial bore to receive a connecting shaft of a scaler tip, such that a working end and a functional shank of the scaler tip are received in a chamber of the housing, with the housing acting as an isolation cage for the scaler tip.

23 Claims, 6 Drawing Sheets

U.S. PATENT DOCUMENTS

2004/0077410 A1    4/2004    Gibbons, Jr. et al.
2004/0134316 A1    7/2004    Loper
2004/0144220 A1    7/2004    Stoick et al.

FOREIGN PATENT DOCUMENTS

EP    1 112 818 A2    7/2001
WO    WO 87/00788    2/1987
WO    WO 2005/102204 A2    11/2005

\* cited by examiner

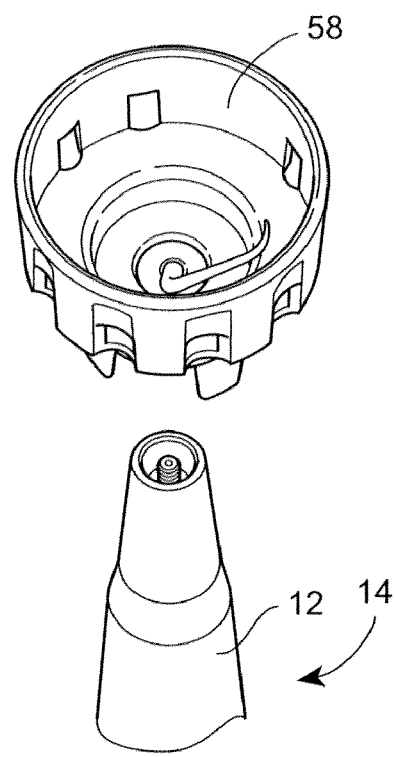
FIG. 14
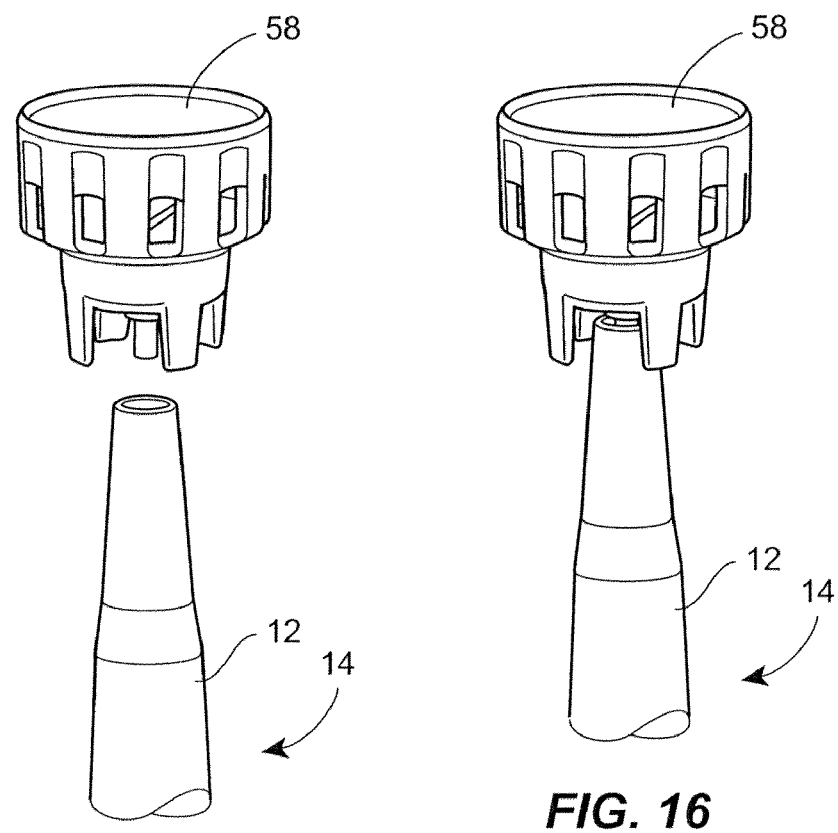
FIG. 15
FIG. 16

US 7,159,494 B2

TORQUE LIMITING WRENCH FOR ULTRASONIC SCALER TIP INSERTION

REFERENCE TO RELATED APPLICATIONS

This application claims priority to, and is entitled to the benefit of the filing date of, U.S. Provisional Patent Application No. 60/635,761, filed Dec. 14, 2004, as to all subject matter commonly disclosed therein.

BACKGROUND

1. Field of the Disclosure

This disclosure relates generally to dental instruments and, more specifically, to apparatus for effecting the replacement of tips of dental hand pieces, such as ultrasonic scalers, in a manner that ensures proper function and avoids damage to either the replacement tip or the handpiece.

2. Related Art

Ultrasonic scalers are used to remove calculus from teeth. A prescribed torque must be exerted when a new tip is inserted in the hand piece to achieve proper installation. A loose tip may detrimentally impact proper function of the device. An over-tightened tip may result in damage to the tip, the hand piece, or both, such as by stripping the threads used to secure the tip within the hand piece of the ultrasonic scaler.

After each use of an ultrasonic scaler, its tips must be sterilized. It is desirable to prevent the tips from colliding with a sterilization tray or with other instruments during sterilization, as such collisions may damage the tips or cause them to prematurely become dull. It would be desirable to provide an apparatus that not only ensured application of the proper amount of torque during tip replacement, but that also serves to protect individual tips during sterilization. Apparatus achieving these and other desired characteristics are described in the following Summary and Detailed Description of the Preferred Embodiments.

SUMMARY OF THE DISCLOSURE

A torque wrench for an ultrasonic scaler comprises a housing, a wrench, a spring, a washer, and a retaining spring. The spring may be provided in the form of, for example, a torsion spring, a leaf spring, or another elastic member providing resistance proportional to deflection thereof.

In order to avoid damage due to the application of an excessive amount of torque during installation of a tip on the hand piece of an ultrasonic scaler, the torque wrench initially rotates while permitting the application of a prescribed amount of torque to be transmitted to the threads of the hand piece onto which the tip is secured. Once the prescribed amount of torque is exceeded, the torque wrench continues to rotate, but does not permit transmission of additional torque to the threads on the hand piece.

BRIEF DESCRIPTION OF THE SEVERAL VIEWS OF THE DRAWING

FIG. 14 is a distal end perspective view of a scaler tip releasably secured in a torque wrench of the present disclosure, prior to initiation of installation of the scaler tip on a hand piece of an ultrasonic dental instrument, shown partially broken away, of an ultrasonic dental instrument;

FIG. 15 is a side perspective view of the torque wrench, sealer tip, and hand piece shown in FIG. 14; and FIG. 16 is a side perspective view similar to FIG. 15, and showing the torque wrench and scaler tip subsequent to initiation of installation of the scaler tip on the hand piece.

DETAILED DESCRIPTION OF THE PREFERRED EMBODIMENTS

Figure 1:
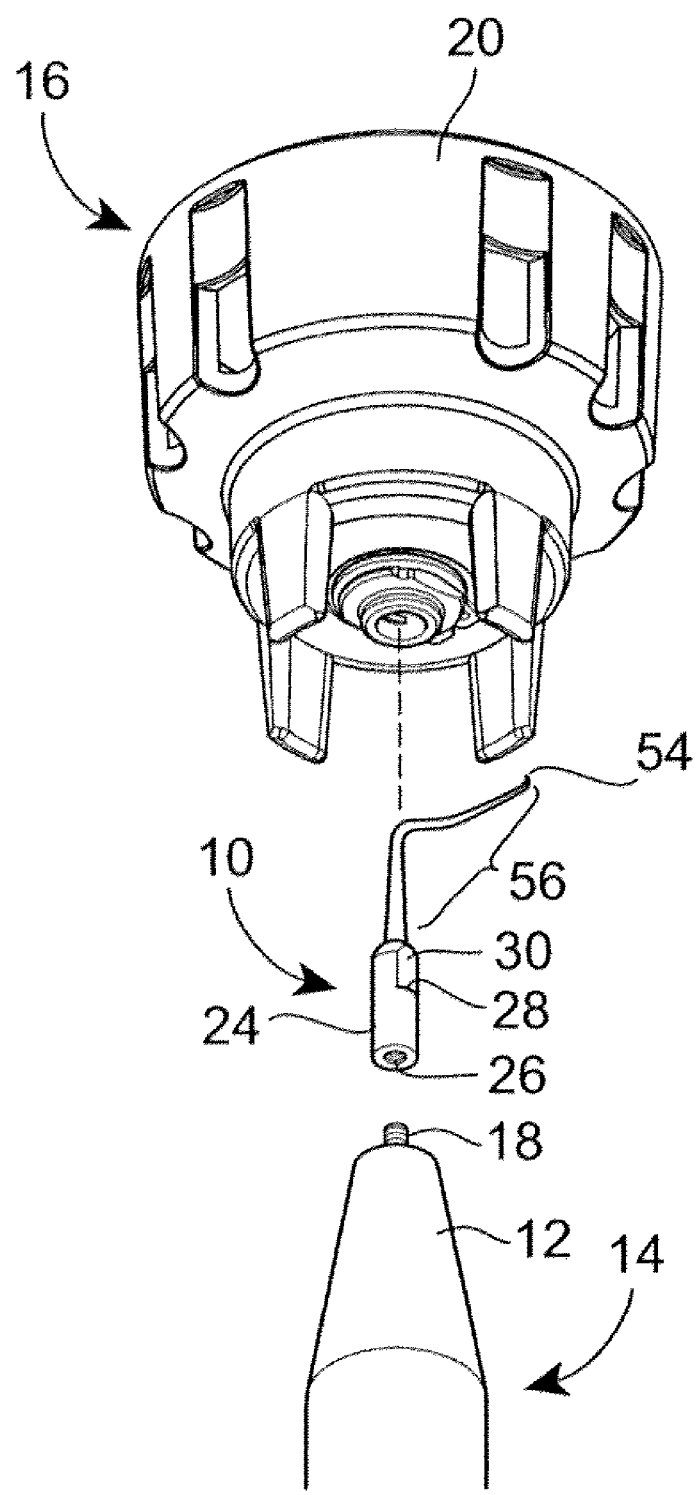
FIG. 1 is a perspective view of a distal portion of a hand piece of an ultrasonic dental instrument having a male threaded end, a scaler tip, and a torque wrench of the present disclosure.

In order to facilitate proper installation of a tip on a hand piece of an instrument, such as a scaler tip 10 on a hand piece 12 of an ultrasonic dental instrument 14, torque wrenches 16 are disclosed herein. The torque wrenches 16 of the present disclosure serves to limit the amount of torque which is transmitted to threads of a male threaded connecting portion 18 of the hand piece 12 onto which the scaler tip 10 is to be secured.

Upon exertion of torque to a housing 20 of a torque wrench 16 of the present disclosure, up to a prescribed or threshold amount, the torque wrench 16 transmits the torque to a core 22 of the torque wrench 16, with which the scaler tip 10 is releasably secured. Such transmission results in exertion of a rotational force on the scaler tip 10, thereby tightening engagement of the scaler tip 10 with the male threaded connection portion 18 of the hand piece 12. Once the prescribed or threshold amount of torque is exceeded, the torque wrench 16 is adapted to cease transmission of torque to the core 22, thereby insulating the scaler tip 10 and male threaded connection portion 18 from excessive loads. The housing 20 of the torque wrench 20 continues to rotate, but the rotation ceases to result in tightening the engagement of the scaler tip 10 with the male threaded connection portion 18 of the hand piece 12.

Figure 2:
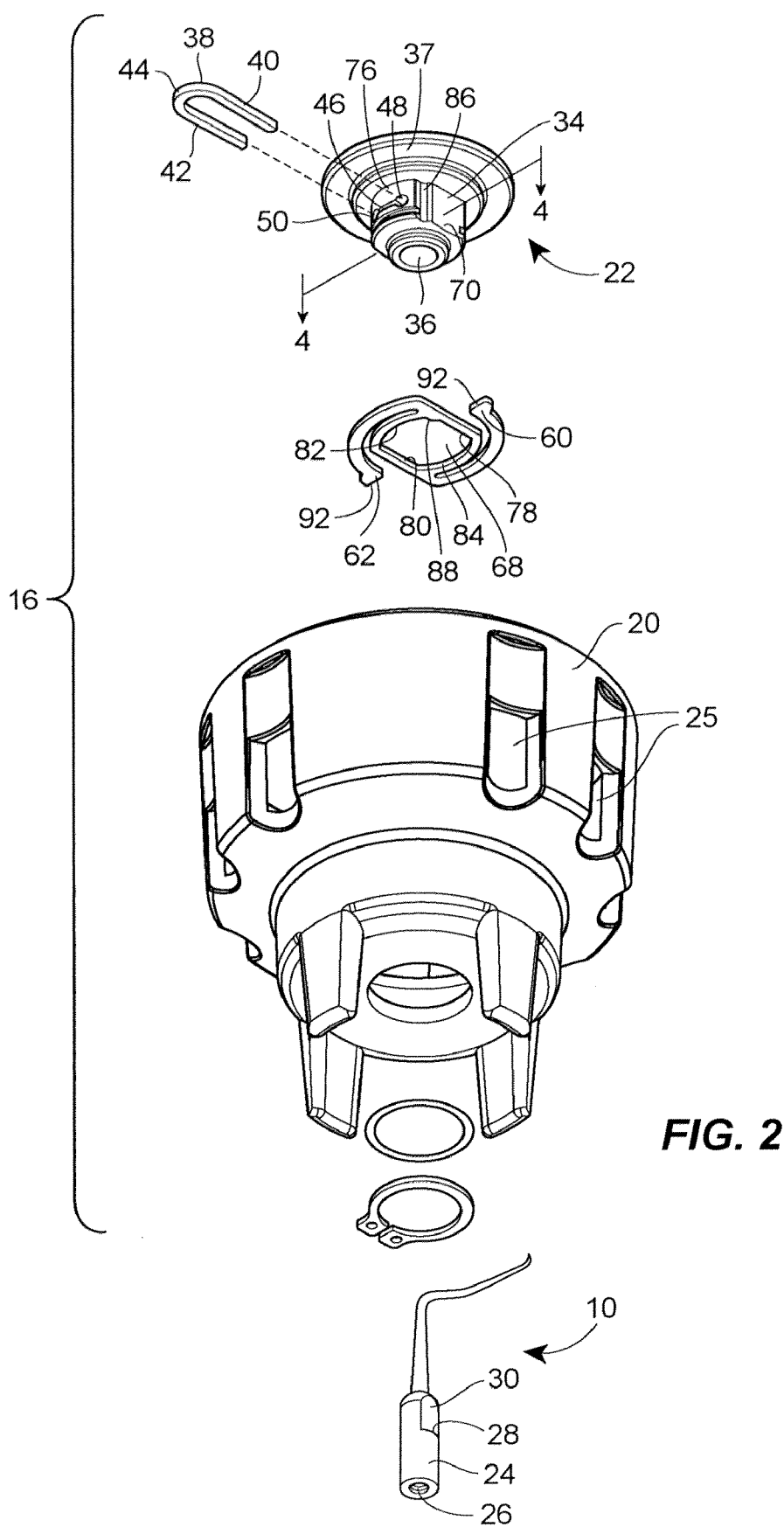
FIG. 2 is an exploded perspective view of the torque wrench of the present disclosure and a scaler tip.
Figure 3:
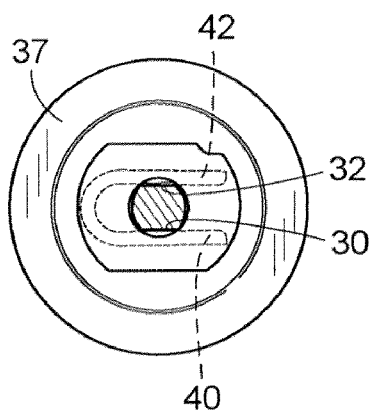
FIG. 3 is an enlarged top view of a core of the torque wrench shown in FIGS. 1 and 2, showing in cross-section a portion of the scaler in releasably secured engagement with the core, and showing in phantom lines a U-shaped retaining spring received in channels provided in the core.
Figure 4:
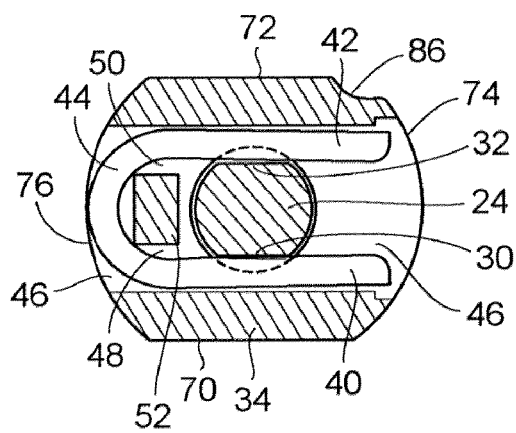
FIG. 4 is an enlarged cross-sectional view, taken along lines 4—4 of FIG. 2, of the core and scaler in releasably secured engagement therewith, and showing the U-shaped retaining spring received in channels provided in the core.
Figure 5:
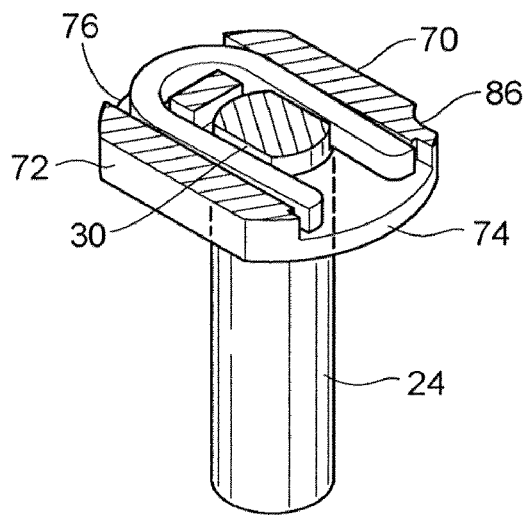
FIG. 5 is an enlarged perspective view of a proximal portion of the core and scaler shown in FIG. 4, and showing the U-shaped retaining spring received in channels provided in the core.
Figure 6:
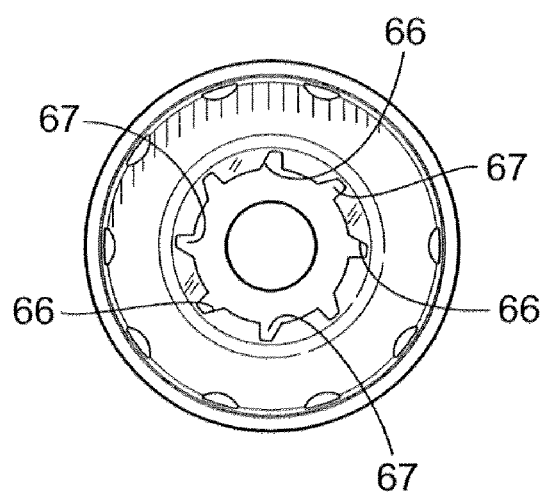
FIG. 6 is a distal end view of a housing of a first embodiment of the torque wrench of the present disclosure.

With reference to FIGS. 1 and 2 of the drawing, the scaler tip 10 is provided with a generally cylindrical main connecting body portion, or connecting shaft, 24, having an internally threaded female opening 26 at a proximal end thereof. The threads of the female opening 26 are complementary to the threads of the male threaded connection portion 18, for threaded engagement therewith. The scaler tip 10 has recessed shoulder portions 28 near a distal end of the connecting shaft 24, with opposing flat surfaces 30, 32 along an exterior of the connecting shaft 24, extending from the recessed shoulder portions 28 to the distal end of the connecting shaft 24.

The opposing flat surfaces 30, 32 along the exterior of the connecting shaft 24 of the scaler tip 10 facilitate selective, releasable securement of the scaler tip 10 to the core 22 of the torque wrench 16. The core 22 has a mounting neck 34 having an axial bore 36 therethrough, and an annular collar 37 at a distal end of the mounting neck 34. As used herein, the terms "proximal" and "distal" are with respect to the hand piece 12. Thus, the distal end of the mounting neck 34 is the end of the mounting neck 34 furthest from the hand piece 12 when the torque wrench 16 is engaged with the hand piece 12. The axial bore 36 may have a diameter slightly greater than an outside diameter of the connecting shaft 24 of the scaler tip 10.

A U-shaped retaining spring 38, having fingers forming first and second legs 40, 42 of the retaining spring 38, and a curved intermediate portion 44, is provided in the core 22 to selectively engage the opposing flat surfaces 30, 32 of the connecting shaft 24 of the scaler tip 10. The U-shaped retaining spring 38 is received in a spring-receiving channel 46 provided in the mounting neck 34 in communication with the axial bore 36. The spring-receiving channel 46 may be disposed in a plane normal to the axial bore 36.

The spring-receiving channel 46 may include a first track 48 sized to receive the first leg 40, and a second track 50 sized to receive the second track 48 of the U-shaped retaining spring 38. The first track 48 and second track 50 may be separated by a post 52. When the U-shaped retaining spring 38 is inserted in the spring-receiving channel 46, an interior of the curved intermediate portion 44 of the retaining spring 38 abuts the post, i.e. is stopped by the post 52, to prevent over-insertion of the retaining spring 38 in the spring-receiving channel 46. The core 22 is received in the housing 20, as explained in more detail below.

To prepare the torque wrench 16 for use with a scaler tip 10 and hand piece 12 of a dental instrument, the connecting shaft 24 of the scaler tip 10 is inserted into a proximal end of the core 22, through the axial bore 36, such that a working end 54 and a functional shank 56 (i.e., that portion between the distal end of the connecting shaft 24 and the working end 54) of the scaler tip 10 are received in a protected chamber 58 within the housing 20 of the torque wrench 16. The opposing flat surfaces 30, 32 along the exterior of the connecting shaft 24 are aligned with the tracks 48, 50 of the spring-receiving channel 46. As the scaler tip 10 is inserted into the core 22, the opposing flat surfaces 30, 32 along the exterior of the connecting shaft 24 come into contact with the respective legs 40, 42 of the U-shaped retaining spring 38.

The initial distance between the first and second legs 40, 42 of the retaining spring 38 is less than the diameter of the connecting shaft 24, and less than the distance between the opposing flat surfaces 30, 32 along the exterior of the connecting shaft 24. As the scaler tip 10 is inserted further into the core 22, using a small amount of axial force, the first and second lets 40, 42 are forced to flex outwardly from one another, permitting the opposing flat surfaces 30, 32 to be received between the first and second legs 40, 42. The flexed first and second legs 40, 42 are biased, by the intermediate portion 44 of the retaining spring 38, back toward one another, thereby loading the retaining spring 38. This restoring force of the retaining spring 38 serves to hold the scaler tip 10 in place. The recessed shoulder portions 28 of the connecting shaft 24 serve as stops when they come into contact with the flexed first and second legs 40, 42, preventing further axial insertion of the scaler tip 10.

In order to limit the amount of torque which is transmitted to threads of the male threaded connecting portion 18 of the hand piece 12 onto which the scaler tip 10 is to be secured, the core 22 may be received in a selective engagement member, such as a cam mechanism 60 having one or more cam follower members 62, 64, each of which selectively engages a series of ramps 66 formed in notches 67 provided in a circular pattern within the housing 20. The mounting neck 34 of the core 22 is mounted within a central aperture 68 of the cam mechanism 60. To facilitate this mounting, the central aperture 68 has a shape complementary to an exterior of the mounting neck 34. As shown, for example, in FIGS. 2 and 7, the exterior of the mounting neck 34 has two opposing flat walls 70, 72, and two curved walls 74, 76. Likewise, the central aperture 68 of the cam mechanism 60 includes two opposing flat walls 78, 80 and two curved walls 82, 84. To ensure proper relative orientation of the cam mechanism 60 and mounting neck 34, a locking groove 86, or keyway, may be provided, such as along a corner of the exterior of the mounting neck 34, and a complementary rib 88, or key, on a respective corner of the central aperture 68. A washer and a retaining ring may be employed to secure the core 22 axially relative to the housing 20, while still permitting rotation of the housing 20 relative to the core 22 when the threshold torque is exceeded.

Figure 7:
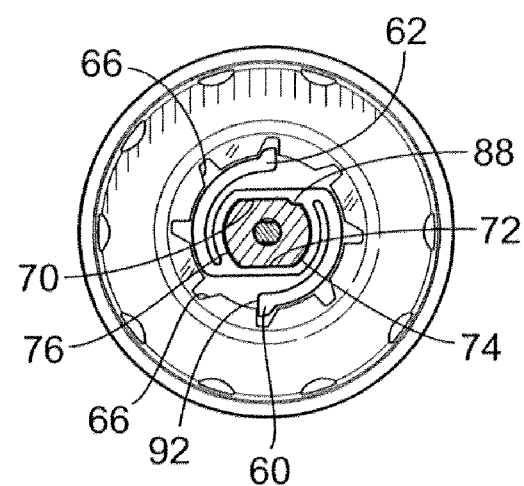
FIG. 7 is a distal end view of the first embodiment of the torque wrench of the present disclosure, with a cam mechanism of the torque wrench received in the housing thereof, and showing in cross section a proximal portion of a core of the torque wrench received in a central opening of the cam mechanism, and a shaft portion of a scaler in secured engagement with the core.
Figure 8:
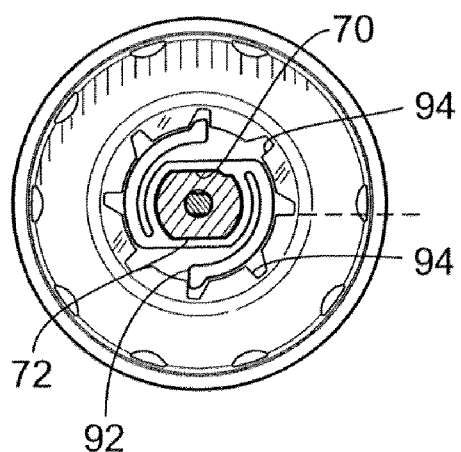
FIG. 8 is a view similar to FIG. 7, and illustrating the relative positions of arms of the cam mechanism to the housing of the torque wrench at a time prior to application of torque in excess of a prescribed or threshold amount.

To facilitate gripping, the housing 20 may be provided with a plurality of indentations 25 around an exterior thereof. Prior to application of torque in excess of a prescribed or threshold amount, the housing 20 of the torque wrench 16 may be rotated in a first direction, and the rotation will be transmitted to the scaler tip 10, with the cam follower members 62, 64 received in the notches 67, as shown in FIGS. 7 and 8, such that when the threads of the internally threaded female opening 26 of the connecting shaft 24 is aligned with the threads of the male threaded connecting portion 18 of the hand piece 12, a threaded engagement between the scaler tip 10 and the hand piece 12 is achieved. Once the scaler tip 10 is either fully engaged with the hand piece 12, or in the event there is some obstruction or mis-alignment of threads, there is resistance to rotation of the housing 20 of the torque wrench 16. At that point, it is desirable to prevent transmission of further torque to the scaler tip 10, as any additional tightening may strip the threads or cause other damage to the scaler tip 10 and/or the hand piece 12.

Figure 9:
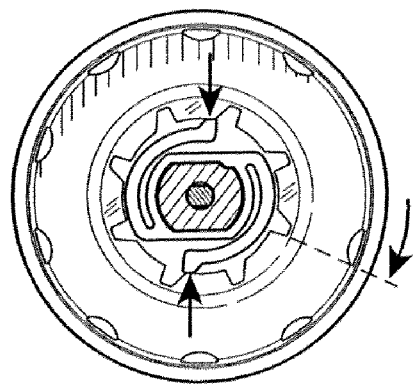
FIG. 9 is a view similar to FIG. 8, and illustrating the relative positions of arms of the cam mechanism to the housing of the torque wrench at a time subsequent to application of torque in excess of a prescribed or threshold amount.
Figure 10:
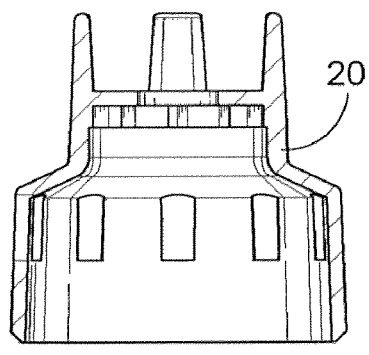
FIG. 10 is a cross-section of a housing of a torque wrench of the present disclosure.
Figure 11:
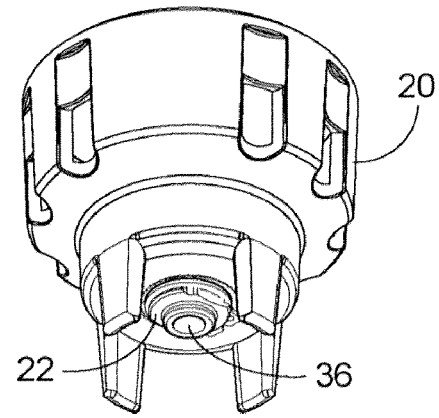
FIG. 11 is a perspective view of the torque wrench shown in FIG. 10, and showing a core of the torque wrench received in the housing thereof.

In order to prevent such further transmission, when the threshold torque is exceeded, upon further rotation of the housing 20 of the torque wrench 16 in the first direction, as indicated in FIG. 9, each of the cam follower members 62, 64 of the cam mechanism 60 rides radially inwardly along a respective one of the ramps 66 until the ramps 66 of the housing 20 override the cam follower members 62, 64. At that point, the cam follower members 62, 64 are flexed inwardly to such an extent that they leave the notches 67. The notches 67 of the housing 20 of the torque wrench 16 are separated by curved surfaces 90 of the housing 20. During further rotation of the housing 20 of the torque wrench 16, the curved surfaces 20 ride along the cam follower members 62, 64, while the cam mechanism 60, the core 22, and the scaler tip 10 remain stationary.

The user may hear an audible clicking sound as the cam follower members 62, 64 reach each successive notch 67, indicating to the user that the threshold torque has been exceeded. If the user is satisfied that the scaler tip is in the desired threaded engagement with the hand piece 12, the torque wrench 16 may then be removed from the hand piece 12, leaving the scaler tip 10 secured to the hand piece 12. If, on the other hand, it is desired to remove the scaler tip 10 from the hand piece 12, the user may simply reverse the direction of rotation of the housing 20 of the torque wrench 16. The cam follower members 62, 64 are each provided with a flat surface 92, which can engage a complementary radially-extending surface 94 in each of the notches 67, arranged opposite the ramp 66 of each of the notches 67. Upon rotation of the housing 20 in a second direction opposite the first direction, the flat surface 92 of each of the cam follower members 62, 64 engage one of the radial-extending surfaces 94. Continued rotation of the housing 20 in the second direction transmits torque to the core 22 and the scaler tip 10, causing the scaler tip 10 to be withdrawn from its threaded engagement with the hand piece 12.

Because the scaler tip 10 may be retained by the first and second legs 40, 42 of the U-shaped retaining spring 38 in a secure relationship with the housing 20, and with the working end 54 and functional shank 56 of the scaler tip 10 received in the chamber 56 of the housing 20, the torque wrench 20 conveniently serves as an isolation cage for use in carrying the scaler tip 10 during sterilization, thereby protecting the scaler tip 10 from damage due to impacts with other instruments undergoing sterilization. When the scaler tip 10 is securely received in the housing 20, the user is protected from being scratched or cut while manipulating the scaler tip 10 during insertion or removal of the scaler tip 10 from a sterilization tray (not shown), or at any other time prior to installation of the scaler tip 10 on the hand piece 12.

Figure 12:
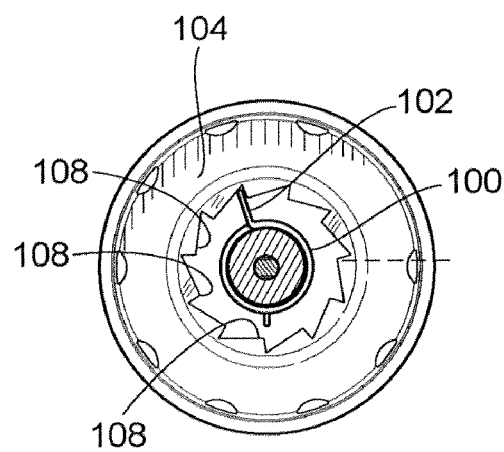
FIG. 12 is a distal end view of a second embodiment of the torque wrench of the present disclosure, with a torsion spring received in the housing thereof, and showing in cross section a proximal portion of a core received in a central opening of the torsion spring, and a shaft portion of a scaler in secured engagement with the core, and illustrating the relative position of an arm of the torsion spring to the housing of the torque wrench at a time prior to application of torque in excess of a prescribed or threshold amount.
Figure 13:
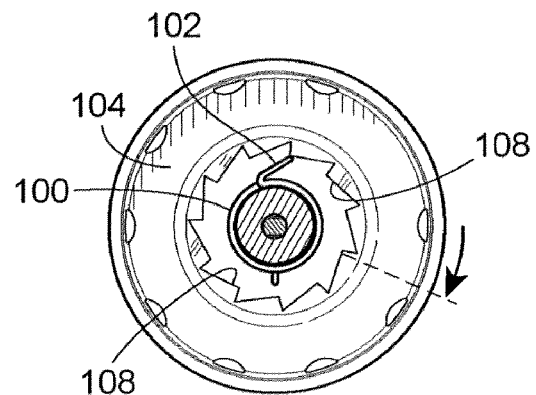
FIG. 13 is a view similar to FIG. 12, and illustrating the relative positions of the arm of the torsion spring to the housing of the torque wrench at a time prior to application of torque in excess of a prescribed or threshold amount.

Turning to FIGS. 12 and 13, an alternate embodiment of the torque wrench 16 is shown, wherein a torsion spring 100 is provided in lieu of the cam mechanism 60. The torsion spring 100 is provided with an extended arm 102, which basically serves the same function as the cam follower members 62, 64 of the cam mechanism 60. The housing 104 of the embodiment of the torque wrench 16 shown in FIGS. 12 and 13 includes a plurality of ramp surfaces 106 arranged on saw teeth 108 provided in a circular pattern within the housing 104.

Upon encountering resistance to tightening of the scaler tip 10 to a hand piece, further rotation of the housing 104 causes one of the ramp surfaces 106 to move relative to the extended arm 102 of the torsion spring 100, causing deflection of the extended arm 102. The friction forces between the extended arm 102 and the saw teeth 108, as well as forces developed within the torsion spring 100 due to the deflection of the extended arm 102, serve to limit the amount of torque applied to the scaler tip.

A plurality of torque wrenches 16 of the present disclosure may be provided as a set, with each torque wrench 16 of the set having a distinguishing characteristic from the others to facilitate differentiation of scaler tips 10 securely received in the respective torque wrenches 16 of the set. For example, each of the torque wrenches 16 of the set may be provided in a different color from any other torque wrenches of the set. By way of example, each torque wrench 16 of the set may have distinguishing indicia on the housing 20 thereof to facilitate differentiation of the scaler tips 10 received in the respective housings 20 from one another. For instance, each housing 20 of the set may include one or more markings on the exterior thereof. The color of the markings of each torque wrench 20 of the set may be unique from any of the other torque wrenches 20 of the set, and the markings may be provided, for example, between recesses 25 the housing 20. Such markings may not only facilitate distinguishing different scaler tips, but may convey additional information to a dental technician associated with the particular scaler tip 10 to be inserted in the torque wrench 16, such as a recommended or preferred power setting to be used on the dental instrument to which the associated scaler tip 10 is installed.

While certain embodiments of a torque wrench for use in the application of scaler tips of hand pieces of dental instruments have been disclosed herein, the appended claims are not limited thereto. For instance, while various forms of a selective engagement member between the core and an interior of the housing, and at least one engagement arm of such selective engagement member received on one of a plurality of ramps within the housing, have been disclosed herein, such as the cam mechanism 60 with cam follower members 62, 64, and the torsion spring 100 with extended arm 102, there are other alternative forms the selective engagement member may take, such as, by way of example only, a leaf spring. Other variations may also be made to the disclosed embodiments that are still within the scope of the appended claims.

We claim:

1. A torque wrench for preventing transmission of excess torque to a connecting shaft of a replaceable instrument tip comprising:

a housing;

a core selectively rotatably engageable with the housing, said core having an axial bore therein and a spring-receiving channel in communication with the axial bore;

a retaining spring received in the channel, said retaining spring selectively securing a connecting shaft of a replaceable instrument tip within the axial bore; and a selective engagement member disposed between the core and an interior of the housing, said selective engagement member including at least one engagement arm in selective communication with one of a plurality of ramps within the housing, and wherein upon application of torque up to threshold level, rotation of the housing causes rotation of the core, and upon application of torque in excess of the threshold level, rotation of the housing causes the at least one engagement arm to lose engagement with one of the ramps, preventing rotation of the core.

2. The torque wrench of claim 1, wherein the channel is disposed in a plane normal to the axial bore.

3. The torque wrench of claim 1, wherein the retaining spring comprises a U-shaped retaining spring.

4. The torque wrench of claim 3, wherein the spring-receiving channel includes a first track and a second track separated from the first track by a post, and wherein a first leg of the U-shaped retaining spring is received in the first track and a second leg of the U-shaped retaining spring is received in the second track.

5. The torque wrench of claim 4, wherein when the U-shaped retaining spring is in the spring-receiving channel, an intermediate portion of the U-shaped retaining spring rests abuts the post.

6. The torque wrench of claim 1, wherein the selective engagement member comprises a cam mechanism having at least two cam following members provided thereon and a central aperture having a shape complementary to an exterior of a mounting neck of the core.

7. The torque wrench of claim 6, wherein the mounting neck of the core has two opposing flat walls and two curved walls, and the central aperture of the cam mechanism has two opposing flat walls and two curved walls.

8. The torque wrench of claim 6, wherein one of the mounting neck of the core and the central aperture of the cam mechanism is provided with a rib and the other of the mounting neck of the core and the central aperture of the cam mechanism is provided with a complementary groove.

9. The torque wrench of claim 8, wherein the rib is provided in a corner of the mounting neck and the complementary groove is provided in a respective corner of the central aperture.

10. A method of installing a replaceable tip on a hand piece of an instrument, comprising:
inserting into an axial bore of a core a replacement tip having a connecting shaft with an internally threaded female recess at a proximal end thereof, a pair of opposing flat surfaces at a distal end of the connecting shaft, each of said opposing flat surfaces terminating at a shoulder of the connecting shaft, said core including a spring-receiving channel in communication with the axial bore;
applying an axial force to the proximal end of the connecting shaft of the replacement tip to force a spring received in said spring-receiving channel into a loaded condition against the connecting shaft, serving to hold the replacement tip in place relative to the core;
providing a selective engagement member between an exterior of the core and one of a plurality of ramps provided on an interior of the housing;
aligning the internally threaded female recess of the connecting shaft with a male threaded connection portion of a hand piece of an instrument; and
applying a torque to the housing to impart rotation of the housing in a first direction until the connecting shaft is secured to the hand piece.

11. The method of claim 10, and applying additional torque to the housing in the first direction beyond a threshold amount required to secure the connecting shaft to the handpiece, whereupon at least one engagement arm of the selective engagement member loses contact with one of the plurality of ramps, facilitating continued rotation of the housing in the first direction while maintaining a stationary position of the connecting shaft relative to the hand piece.

12. The method of claim 10, wherein in providing the selective engagement member between an exterior of the core and one of a plurality of ramps provided on an interior of the housing, the selective engagement member is a cam mechanism including at least two cam follower members.

13. The method of claim 12, and inserting a mounting neck of the core through a central aperture of the cam mechanism.

14. The method of claim 13, and prior to inserting the mounting neck of the core through the central aperture of the cam mechanism, aligning two opposing flat walls of the mounting neck of the core with two opposing flat walls of the central aperture of the cam mechanism.

15. The method of claim 14, and in aligning the two opposing flat walls of the mounting neck of the core with two opposing flat walls of the central aperture of the cam mechanism, aligning a rib provided along one of the mounting neck of the core and the central aperture of the cam mechanism with a complementary groove provided along the other of the mounting neck of the core and the central aperture of the groove.

16. The method of claim 10, wherein in providing the selective engagement member between an exterior of the core and one of a plurality of ramps provided on an interior of the housing, the selective engagement member is a torsion spring.

17. A torque wrench for preventing transmission of excess torque to a connecting shaft of a replaceable instrument tip comprising:
a housing having
a chamber for receiving a working end of a scaler tip;
a plurality of ramps arranged in a circular fashion in an interior of the housing; and
a plurality of recesses in an exterior of the housing;
a core selectively rotatably engageable with the housing, said core having a mounting neck with an axial bore therethrough and an annular collar at a distal end of the mounting neck; and
a selective engagement member disposed between the mounting neck of the core and the plurality of ramps of the housing, the selective engagement member including at least one engagement arm in selective communication with one of the ramps.

18. The torque wrench of claim 17, wherein the selective engagement member is a cam mechanism having at least two cam follower members, each of which disengages from one of the ramps upon application of a torque to the housing beyond a threshold level.

19. The torque wrench of claim 17, wherein the cam mechanism includes a central aperture therein having a shape complementary to an exterior of the mounting neck of the core.

20. The torque wrench of claim 17, wherein the selective engagement member is a torsion spring.

21. The torque wrench of claim 17, wherein the torque wrench further includes a distinguishing characteristic to facilitate differentiation of an associated scaler tip from scaler tips associated with other torque wrenches.

22. The torque wrench of claim 21, wherein the distinguishing characteristic includes distinguishing indicia on the exterior of the housing.

23. The torque wrench of claim 22, wherein the distinguishing indicia includes a color marking on the exterior of the housing.

* * * * *